US008942457B2

(12) United States Patent
Florent et al.

(10) Patent No.: US 8,942,457 B2
(45) Date of Patent: Jan. 27, 2015

(54) NAVIGATING AN INTERVENTIONAL DEVICE

(75) Inventors: Raoul Florent, Ville Davray (FR); Gert Antonius Franciscus Schooenenberg, Odiliapeel (NL); Bram Antonius Philomena Van Rens, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 230 days.

(21) Appl. No.: 13/521,237

(22) PCT Filed: Jan. 4, 2011

(86) PCT No.: PCT/IB2011/050010
§ 371 (c)(1),
(2), (4) Date: Jul. 10, 2012

(87) PCT Pub. No.: WO2011/086475
PCT Pub. Date: Jul. 21, 2011

(65) Prior Publication Data
US 2013/0101196 A1   Apr. 25, 2013

(30) Foreign Application Priority Data

Jan. 12, 2010 (EP) ..................................... 10305029

(51) Int. Cl.
*G06K 9/00* (2006.01)
*G06T 11/00* (2006.01)
(Continued)

(52) U.S. Cl.
CPC ............. *G06T 11/003* (2013.01); *G06T 7/0024* (2013.01); *G06T 11/008* (2013.01);
(Continued)

(58) Field of Classification Search
USPC ......... 382/100, 128, 129, 130, 131, 132, 133, 382/154, 285; 128/922; 378/4–27; 345/419–427; 348/578–580
See application file for complete search history.

(56) References Cited

U.S. PATENT DOCUMENTS 5,891,030 A * 4/1999 Johnson et al. ............... 600/407
(Continued)

FOREIGN PATENT DOCUMENTS

EP    0809211    11/1997
(Continued)

OTHER PUBLICATIONS

D. Ruijters, et al., "Vesselness-Based 2D-3D Registration of the Coronary Arteries", International Journal of Computer Assisted Radiology and Surgery, Springer Berlin/Heidelberg, vol. 4, No. 4, Jun. 2009, Abstract.
(Continued)

*Primary Examiner* — Anand Bhatnagar

(57) ABSTRACT

The present invention relates to navigating an interventional device. In particular, the invention relates to a system for navigating an interventional device within a tubular structure of an object, a method for navigating an interventional device within a tubular structure of an object as well as a computer program element and a computer-readable medium. In order to provide enhanced information to the user in an easily comprehensible manner while keeping the X-ray dose to a minimum, a system and a method for navigating an interventional device within a tubular structure of an object are provided, wherein the method comprised the following steps: a) Acquiring 2D X-ray fluoroscopy image data in one projection geometry of a region of interest of the tubular structure; b) detecting the interventional device in the 2D X-ray image; c) determining the 2D position of the interventional device in the 2D X-ray image; d) registering the at least one 2D X-ray image with a previously acquired 3D dataset of the region of interest of the tubular structure; e) mapping the determined 2D position of the interventional device to a position in the 3D dataset; f) extracting local 3D parameters of the tubular structure at the position of the interventional device; g) generating navigational information on behalf of the determined 3D position of the interventional device and the extracted local 3D parameters; and h) providing the navigational information to the user.

12 Claims, 12 Drawing Sheets

(51) Int. Cl.
*G06T 7/00* (2006.01)
*A61B 6/00* (2006.01)

(52) U.S. Cl.
CPC ........ *A61B 6/52* (2013.01); *G06T 2207/10072* (2013.01); *G06T 2207/10121* (2013.01); *G06T 2207/30101* (2013.01); *G06T 2211/404* (2013.01); *G06T 2211/428* (2013.01); *Y10S 128/922* (2013.01)
USPC .............................. 382/132; 128/922; 378/6

(56) References Cited

U.S. PATENT DOCUMENTS

| | | | |
|---|---|---|---|
| 6,490,475 | B1 | 12/2002 | Seeley et al. |
| 6,711,433 | B1 | 3/2004 | Geiger et al. |
| 7,010,080 | B2 * | 3/2006 | Mitschke et al. ................. 378/8 |
| 7,519,414 | B2 * | 4/2009 | Mitschke et al. ............. 600/424 |
| 7,570,791 | B2 * | 8/2009 | Frank et al. ................... 382/132 |
| 7,590,442 | B2 * | 9/2009 | Boese et al. ................... 600/424 |
| 7,889,905 | B2 * | 2/2011 | Higgins et al. ................ 382/130 |
| 8,675,996 | B2 * | 3/2014 | Liao et al. .................... 382/294 |
| 2005/0015006 | A1 * | 1/2005 | Mitschke et al. ............. 600/431 |
| 2007/0100223 | A1 * | 5/2007 | Liao et al. .................... 600/407 |
| 2007/0189457 | A1 * | 8/2007 | Deinzer ...................... 378/98.12 |
| 2007/0231605 | A1 | 10/2007 | Watkins |
| 2008/0089566 | A1 | 4/2008 | Node-Langlois et al. |
| 2008/0144866 | A1 | 6/2008 | Barthel et al. |
| 2009/0281418 | A1 * | 11/2009 | Ruijters et al. ................ 600/424 |

FOREIGN PATENT DOCUMENTS

| | | |
|---|---|---|
| JP | 8332191 | 12/1996 |
| JP | 2009106502 | 5/2009 |
| JP | 2012054571 | 3/2012 |
| WO | WO2005073917 | 8/2005 |
| WO | WO2006103644 | 10/2006 |
| WO | WO2007113705 | 10/2007 |
| WO | WO2008001264 | 1/2008 |
| WO | WO2008050316 | 5/2008 |

OTHER PUBLICATIONS

H. Sundar, et al., "A Novel 2D-3D Registration Algorithm for Aligning Fluoro Images with 3D Pre-Op CT/MR Images", Siemens Corporate Research, 755 College Road East, Princeton, NJ, USA 08540, Section for Biomedical Image Analysis, University of PA, 3600 Market St., Suite 380, Philadelphia, PA USA, 19104, pp. 1-7.

* cited by examiner

NAVIGATING AN INTERVENTIONAL DEVICE

FIELD OF THE INVENTION

The present invention relates to navigating an interventional device. In particular, the invention relates to a system for navigating an interventional device within a tubular structure of an object, a method for navigating an interventional device within a tubular structure of an object as well as a computer program element and a computer-readable medium.

BACKGROUND OF THE INVENTION

In order to use interventional devices in tubular structures where the location of the device is not visible to the user from the outside of the object, the user is provided with information about the location of the device in relation to the object. For example, during neurological interventions, devices are routinely used in the treatment process of diseased vessels. In order to assist the physician, for example a neurosurgeon, with navigating a specific device to the diseased vessel segment, the device and region of interest are visualized using X-ray imaging. For example, this is achieved by two-dimensional X-ray projection images, a disadvantage of which is that the true three-dimensional nature of the vessels is lost. This may lead to distorted visualization of, for example, vessel segment length, vessel branching angles and vessel tortuosity. This may hamper navigation of the device through the vessels. An example for applying information for navigation purposes is the so-called road mapping functionality. From an available 3D vessel representation, a projection image that matches the current viewing angle of the X-ray apparatus is created. This artificial projection image is then overlaid and registered on live X-ray fluoro images to provide the physician with the road map during device navigation. For example, EP 0 809 211 A2 describes to form and store a series of 2D X-ray images of an object, to form a 3D image, to extract a relevant structure from the 3D image and to calculate a series of the synthetic 2D projection images of the extracted structure, wherein the structure is projected with the same geometrical parameters as used for the structure during the formation of the individual X-ray images. Further, the synthetic projection images and the processed X-ray images are superimposed.

SUMMARY OF THE INVENTION

However, the projected roadmap is still a 2D "flat" representation of the vessels which does not provide depth information. Additionally, overlaying the footprint of the vessels tends to clutter the interventional image, which should be left as clean as possible. Further, it is a constant demand to provide detailed enhanced information.

Hence, there may be a need to provide enhanced information to the user, i.e. the operator, in an easily comprehensible manner.

According to an exemplary embodiment of the invention, the method and a system for navigating an interventional device within a tubular structure of an object is provided as further defined in the independent claims.

According to an exemplary embodiment of the invention, a method for navigating an interventional device within a tubular structure of an object is provided, comprising the following steps: a) acquiring 2D X-ray fluoroscopy image data in one projection geometry of a region of interest of the tubular structure; b) detecting the interventional device in the 2D X-ray image; c) determining the 2D position of the interventional device in the 2D X-ray image; d) registering the at least one 2D X-ray image with a previously acquired 3D dataset of the region of interest of the tubular structure; e) mapping the determined 2D position of the interventional device to a position in the 3D dataset; f) extracting local 3D parameters of the tubular structure at the position of the interventional device; g) generating navigational information on behalf of the determined 3D position of the interventional device and the extracted local 3D parameters; and h) providing the navigational information to the user.

One of the advantages is that, although only one projection is provided for the X-ray fluoroscopy image, which one projection for itself does not provide any depth information, by mapping the determined two-dimensional position to a position in the 3D data set it is still possible to derive the necessary three-dimensional information as a basis for the navigational information being provided to the user. The navigational information can thus assist the user, for example a physician, to steer the device navigation, for example. By extracting local three-dimensional parameters, the interventional device serves as a pointer in the 3D data set or 3D volume. Since the two-dimensional information is acquired by two-dimensional X-ray fluoroscopy images, it is possible to continuously acquire such images in order to continuously track the two-dimensional device position and the related three-dimensional position during the navigation process, providing the possibility to communicate three-dimensional information to the physician, or the user, in real-time.

For example, a neurosurgeon performs X-ray angiography on patients to investigate and diagnose neurology related diseases, for example in the head region of a patient. For example, the neurosurgeon performs a diagnostic rotational angiographic scan. From the two-dimensional projection images acquired with this scan, a three-dimensional representation of the neuro vessels is created, which vessels show a high tortuosity. This three-dimensional representation can, for example, be used to support the diagnosis based on the two-dimensional angiograms. The three-dimensional representation may also be acquired on a different imaging system, for example a CT scanner. When treatment of the patient is necessary, a device is navigated to the diseased vessel segment. The device steering is done under the guidance of X-ray fluoroscopy. In order to benefit from the three-dimensional vessel information already available, the three-dimensional volume needs to be registered to the fluoro images of the device and the vessels, for example the neuro vessels. Registration can, for example, be achieved by using the X-ray systems geometry information, and fluoro images of the neuro vessels enhanced with contrast agent. The three-dimensional volume can be, but does not need to be segmented, for example, registration can be done by matching ridgeness information in the two-dimensional fluoro and three-dimensional volume. During device navigation, the device is detected and tracked in the fluoroscopy images such that its position in the fluoro images is continuously known. This position is then continuously mapped to a unique position in the registered three-dimensional representation of the vessel. Three-dimensional information of the vessel segment surrounding the device location can then be presented, for example displayed on a screen, to a neurosurgeon to support navigation of the device.

The invention can be used in X-ray guided neuro vessels interventions, as described above. However, the invention can also be applied in any X-ray guided intervention in which at least to some extent radiopaque devices are used and three-dimensional information on the region of interest is available.

Since the two-dimensional X-ray fluoroscopy images are acquired in only one projection geometry, the navigational information is based on a computed determination of a point in the three-dimensional data set for which the assumption that the point of the device is located within a segment of the tubular structure has the highest plausibility.

According to an exemplary embodiment of the invention, a system for navigating an interventional device within a tubular structure of an object is provided, the system comprising: an X-ray image acquisition device; a processing unit; and an interface. The X-ray image acquisition device is adapted to acquire 2D X-ray fluoroscopy image data in one projection geometry of a region of interest of the tubular structure. The processing unit is adapted to detect the interventional device in the 2D X-ray image and to determine the 2D position of the interventional device in the 2D X-ray image. The processing unit is further adapted to register the at least one 2D X-ray image with a previously acquired 3D dataset of the region of interest of the tubular structure and to map the determined 2D position of the interventional device to a position in the 3D dataset. The processing unit is also adapted to extract local 3D parameters of the tubular structure at the position of the interventional device and to generate navigational information on behalf of the determined 3D position of the interventional device and the extracted local 3D parameters. The interface is adapted to provide the navigational information to the user.

According to an exemplary embodiment of the invention, the navigation of an interventional device comprises guiding a user, for example a physician such as a surgeon or interventional cardiologist performing a medical procedure.

According to an exemplary embodiment of the invention, the 2D X-ray fluoroscopy image data comprises a sequence of two images with the same projection geometry. The 3D position is mapped by extracting a determined point of the interventional device in the two 2D images.

According to an exemplary embodiment of the invention, a point on the device corresponds to a single line in 3D space and the same physical point on the device is followed along several frames, thus creating several temporally-dependent 3D lines.

According to an exemplary embodiment of the invention, several physical points on the same device and at a given instant are used creating several spatially-dependent 3D lines.

According to an exemplary embodiment of the invention, a combination of both methods is provided, i.e. several physical points on the device are tracked along time.

According to an exemplary embodiment of the invention, to a given point seen in a projection, there is a set of possible 3D points that have created the 2D projected point, i.e. for a given geometry. This set is a 3D line. All the points on this line participate to the projection, but in case only some of them are really radio-absorbent, according to the invention, those very absorbent points are referred to as the 3D originating points of the 2D projected point.

For example, a line in space potentially may intersect several segments of the tubular structure, for example in several vessels. More points are acquired, for example, temporal or spatial different points. Ambiguity is thus removed by determining which segment, or vessel, has the highest probability to enclose the device.

According to an exemplary embodiment of the invention, the one projection geometry is a monoplane X-ray fluoroscopy acquisition.

According to an exemplary embodiment of the invention, the device lies within a segment of the tubular structure throughout the navigational procedure.

According to an exemplary embodiment of the invention, the device can only lie within a couple of possible tubular segments. Further, the probability is maximized by the number of intersections of determined device lines and tubular segments; wherein the intersections correspond to points.

According to an exemplary embodiment of the invention, the device has a tip and the tip is localized in the tubular structure complexity with an accuracy of about or less that the tubular width, for example, unless the device is bent and leaning against either side of the tubular segment.

According to an exemplary embodiment of the invention, the tip is localized in the tubular structure complexity in the length direction of the tubular segment and not within the width direction.

According to an exemplary embodiment of the invention, the interventional device is at least partially radiopaque to X-rays.

According to an exemplary embodiment of the invention, the interventional device is a guide wire.

According to an exemplary embodiment of the invention, the interventional device is a endo-prosthesis delivery system such as a stent delivery system with its balloon and locating markers. This kind of devices might be used in coronary or Neuro interventions (Neuro stents, flow diverters, coils).

According to an exemplary embodiment of the invention, the tubular structure comprises vessels.

According to an exemplary embodiment of the invention, navigation is provided in 2D.

According to an exemplary embodiment of the invention, the tubular structure provides only a few locations in space for the interventional device to be enclosed within the tubular structure which, for example, has a sparse structure.

According to an exemplary embodiment of the invention, the 3D dataset is created from acquired 2D projections, for example X-ray angiograms. For example, the 2D projections are acquired in form of a rotational angiographic scan.

According to an exemplary embodiment of the invention, the 3D dataset or 3D representation is acquired from a CT scanner, MRI, ultrasound or the like.

According to an exemplary embodiment of the invention, the at least one 2D X-ray image is registered such that the spatial orientation and position of the 3D volume of the 3D dataset corresponds to the spatial orientation and position of the tubular structure of the object of interest in the X-ray.

According to an exemplary embodiment of the invention, for registration, ridgeness information in the 2D image and in the 3D volume is matched.

According to an exemplary embodiment of the invention, for registration, also the X-ray system's geometry information is used.

According to an exemplary embodiment of the invention, the 2D X-ray fluoroscopy image data is acquired with injected contrast agent.

According to an exemplary embodiment &the invention, the 2D device position and related 3D position are continuously tracked during the navigation process and navigational information is provided to the user in real-time.

According to an exemplary embodiment of the invention, the local 3D parameters comprise parameters of the tubular segment of the tubular structure surrounding the interventional device.

For example, in case the tubular structure comprises vessels, the local 3D parameters comprise quantities typically derived with quantitative coronary analysis (QCA), like vessel diameter, lumen area, segment length and bifurcation angles.

Depending on the type of interventional procedure, an addition to three-dimensional parameters, also other local parameters relating to the determined point in space of the tubular structure can also be provided as additional information to the user. For example, characteristics or features of the vessel walls, for example tissue like calcifications, can also be indicated or transmitted as information to the user.

According to an exemplary embodiment of the invention, the local 3D parameters comprise parameters of the tubular structure in the vicinity of the interventional device.

According to an exemplary embodiment of the invention, the local 3D parameters comprise parameters of the tubular structure in as spatial region around the interventional device.

According to an exemplary embodiment of the invention, the extension of the spatial region is predetermined.

According to an exemplary embodiment of the invention, the extension is predetermined according to the chosen device.

According to an exemplary embodiment of the invention, the extension is set by a user.

According to an exemplary embodiment of the invention, step h) comprises displaying the navigational information to the user.

According to an exemplary embodiment of the invention, the local 3D parameters of the tubular structure are extracted from the previously acquired 3D dataset.

According to an exemplary embodiment of the invention, step e) comprises computing probabilities for different segments of the tubular structure; and maximizing accumulated probability from the different probabilities to determine in which segment of the tubular structure the device may be located. Further, on behalf of the accumulated probability information is gathered in space from the 3D dataset.

In order to map the 2D position to a position in the 3D data set, or in other words to find a 3D position for the 2D position, the chance or possibility for the two-dimensional position is computed by transforming the two-dimensional position into a line in the 3D data set. Then, the probability or chance for a point along the line to be the actual 3D position is computed by reducing the possible positions along the line to be matching with one of the tubular segments that are defined in the 3D data set. Of course, this leads to numerous several segments into which the device can fit. For example, if this is followed in time, the probability for several vessels is maximized thus leading to accumulated probabilities.

In other words, a number of computational steps or procedures, comprising several probability computation loops, provide geometrical information with a maximized probability to represent the actual three-dimensional position.

According to an exemplary embodiment of the invention, a device which is point-wise visible under X-ray fluoroscopy is temporally detected as two different points; and in step e) probabilities are computed for the points to be located in a number of segments of the tubular structure and the probabilities are maximized to reduce the number of segments. Further, a segment with the highest probability is determined to be enclosing the device.

According to an exemplary embodiment of the invention, before step h), the navigational information is converted into graphical advisory information. Further, step h) comprises adapting acquired image data of the region of interest on behalf of the navigational information and displaying the adapted image data to the user.

According to an exemplary embodiment of the invention, the 2D X-ray image data is transformed into enhanced 2D image data by superimposing the graphical advisory information with the 2D X-ray image data and the enhanced 2D image data is displayed to the user.

According to an exemplary embodiment of the invention, the navigational information is provided to the user while displaying the acquired 2D X-ray image.

According to an exemplary embodiment of the invention, 3D information is shown in 2D images.

According to an exemplary embodiment of the invention, 3D image data is generated from the previously acquired 3D dataset and the 3D image data is transformed into enhanced 3D image data by integrating the graphical advisory information. Further, the enhanced 3D image data is displayed to the user.

According to an exemplary embodiment of the invention, step f) comprises determining the orientation of the surrounding tubular structure; step g) comprises determining the orientation of the device in relation to the surrounding tubular structure; and step h) comprises displaying an orientation indicator.

For example, when guiding a catheter or a wire tip through a vessel tree, it is important to get a good perception of the local vessel shape in three dimensions, in particular when confronted to strong out of plane bending or complex tortuosity. The usual three-dimensional road mapping technique provides a good projected road map in the X-ray fluoro plane, but is without depth information or at least less informative when it comes to the depth direction. When back-projecting the device into the 3D reconstructed vessel tree, the disadvantage is that this entails referring to a reconstructed and somewhat artificial viewing mode. Another serious problem is that three-dimensional data and two-dimensional projecting live views do not fuse very easily or naturally. By providing a very simple depth indication, such as an orientation vector, at the device location, this using of a device as a pointer to 3D data leads to a visualization that can easily be blended with the live image and does not clutter the fluoroscopy plane, which can thus stay as clear and unambiguous as possible. Another advantage is that, apart from the device tracking and registration steps already mentioned, one has simply to get orientation information from the three-dimensional data which does not require actual segmentation. This provides advantages concerning computational power and time required in the system.

According to an exemplary embodiment of the invention, the orientation indicator is a depth indicator indicating the depth of the tubular structure.

According to an exemplary embodiment of the invention, the orientation indicator is an orientation vector.

According to an exemplary embodiment of the invention, the navigational information comprises information about the tubular structure, for example one or several of the group of diameter, lumen area, tissue, segment length, bifurcation positions and bifurcation angles.

According to an exemplary embodiment of the invention, these tubular parameters are derived by segmenting the tubular structure and surrounding structures.

According to an exemplary embodiment of the invention, the segmentation is performed with the 3D dataset or 3D volume beforehand.

According to an exemplary embodiment of the invention, the segmentation is performed on the spot using the device location in the 3D dataset as a trigger for local automatic tubular structure segmentation.

According to an exemplary embodiment of the invention, step g) comprises transforming the determined 3D parameters of the tubular structure into graphical information; and step h) comprises displaying the graphical information.

According to an exemplary embodiment of the invention, step g) comprises identifying optimal viewing direction for the segment of the tubular structure surrounding the interventional device; determining a deviation factor of current viewing direction of the X-ray imaging device in relation to the optimal viewing direction; and determining a movement factor for optimal viewing; and step h) comprises moving the X-ray imaging device in relation to the object for optimal viewing.

Having an optimal view angle of the device which is being navigated through, for example, a vascular structure decreases the chance of misinterpretation on the side of the user due to a minimally foreshortened or even unforeshortened view in which no or at least only a minimum number of vessels overlap. For example, in case of a C-arm, the C-arm needs to be positioned manually by the operator for an optimal view. This requires full concentration and also experience by the user which has further disadvantages with respect to the duration of an interventional procedure. For example, the derived optimal viewing angle can be used to steer the C-arc of an X-ray system to the optimal viewing angle of the vessel segment pointed to by the device. This would then facilitate the interventional procedure, because the information to the user would be presented in an optimized way, i.e. better detectable and easier readable image information. This also means relieve for the user, since he or she can grasp the information in a shorter time, thus providing certain economical benefits.

For example, when navigating the guide wire through neuro vessels to the region of interest, the guide wire tip can be used as a pointer. During the neuronavigation process, the C-arc can be steered in real-time through the optimal viewing angles of the vessel segments through which the tip advances. In that way, for example, a good view of the device can be maintained while patient dose can be reduced.

According to an exemplary embodiment of the invention, the optimal viewing direction is identified for the determined 3D position of the interventional device with respect to the tubular structure.

According to an exemplary embodiment of the invention, the X-ray imaging device and the object are moved in relation to each other according to the determined movement factor to acquire further 2D X-ray fluoroscopy image data.

According to an exemplary embodiment of the invention, the X-ray imaging device is steered to the optimal viewing angle.

According to an exemplary embodiment of the invention, the X-ray imaging device is a C-arm and wherein for the optimal viewing direction a rotating or viewing angle is determined as determined movement factor; and the C-arm is rotated according to viewing angle to acquire further 2D X-ray fluoroscopy image data.

According to an exemplary embodiment of the invention, in an optimal viewing direction, foreshortening of the tubular structure at the location of the device position is minimal.

According to an exemplary embodiment of the invention, in an optimal viewing direction, overlap of the tubular structures at the location of the device position is minimal.

According to an exemplary embodiment of the invention, in an optimal viewing direction, the X-ray dose to the patient and/or the clinical staff is minimal.

According to an exemplary embodiment of the invention, the optimal viewing angle is defined by different parameters which parameters are being weighed differently depending on the phase of the interventional procedure.

According to an exemplary embodiment of the invention, during guide wire navigation, the dose parameters have the largest weight whereas during lesion treatment, foreshortening and overlap have the largest weight.

According to an exemplary embodiment of the system according to the invention, the processing unit is adapted to convert the navigational information into graphical advisory information. The processing unit is also arranged to adapt acquired image data of the region of interest on behalf of the navigational information. A display is connected to the interface, the display being adapted to display the adapted image data to the user.

According to an exemplary embodiment of the invention, the processing unit is adapted to transform the 2D X-ray image data into enhanced 2D image data by superimposing the graphical advisory information with the 2D X-ray image data. The display is arranged to display the enhanced 2D image data.

According to an exemplary embodiment of the invention, the processing unit is adapted to generate 3D image data from the previously acquired 3D dataset and to transform the 3D image data into enhanced 3D image data by integrating the graphical advisory information. The display is arranged to display the enhanced 3D image data.

According to an exemplary embodiment of the invention, the processing unit is adapted to determine the orientation of the surrounding tubular structure; and to determine the orientation of the device in relation to the surrounding tubular structure. The display is arranged to display an orientation indicator.

According to an exemplary embodiment of the invention, the processing unit is adapted to identify optimal viewing direction for the segment of the tubular structure surrounding the interventional device and to determine a deviation factor of current viewing direction of the X-ray imaging device in relation to the optimal viewing direction. The processing unit is further adapted to determine a movement factor for optimal viewing. The X-ray image acquisition device is adapted to be moved in relation to the object for optimal viewing.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

BRIEF DESCRIPTION OF THE DRAWINGS

The aspects defined above and further aspects, features and advantages of the present invention can also be derived from the examples of embodiments to be described hereinafter and are explained with reference to examples of embodiments, but to which the invention is not limited. The invention will be described in more detail hereinafter with reference to the drawings.

DETAILED DESCRIPTION OF EMBODIMENTS

Figure 1:
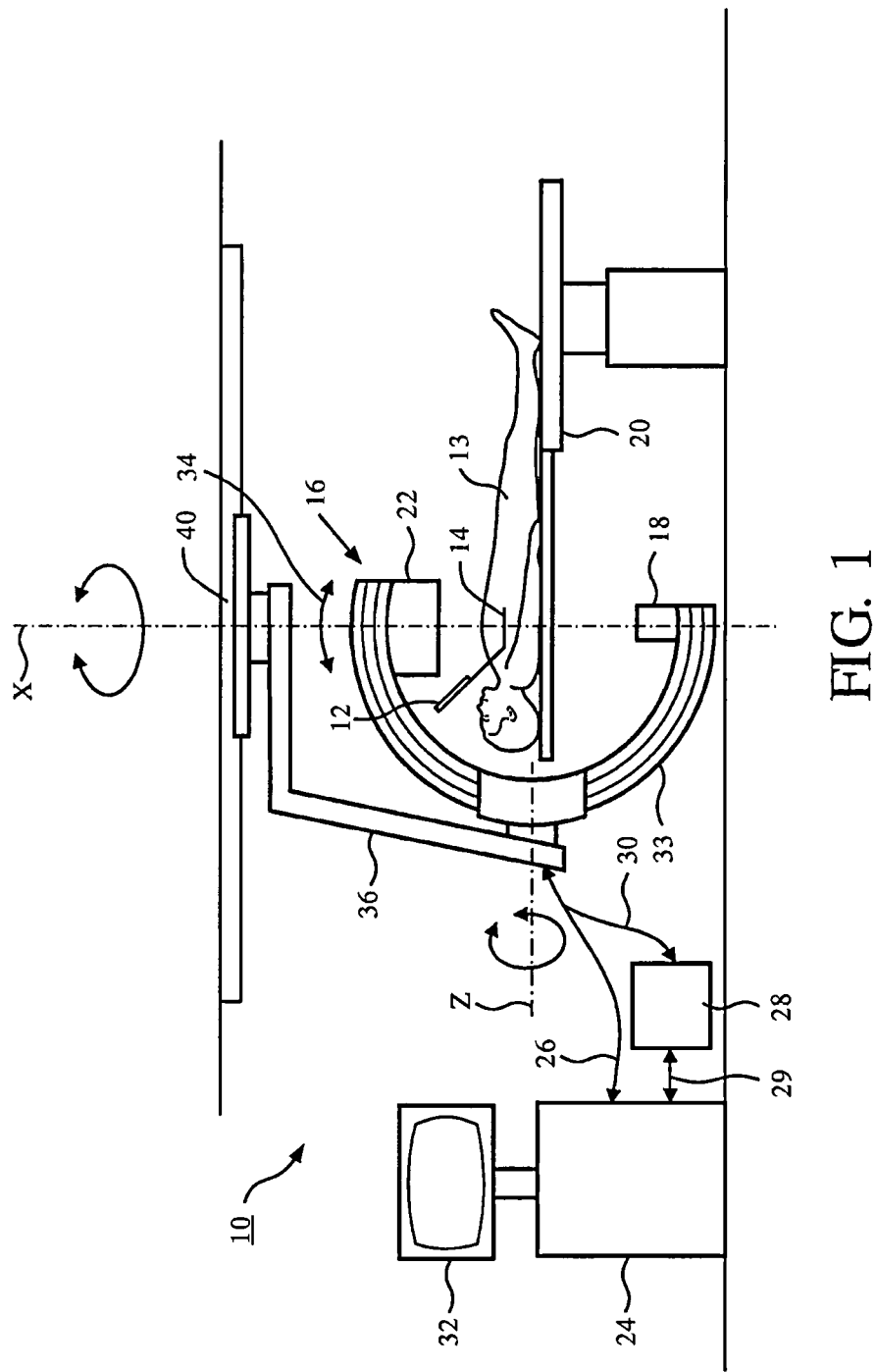
FIG. 1 schematically shows a system for navigating an interventional device according to the invention.
Figure 2:
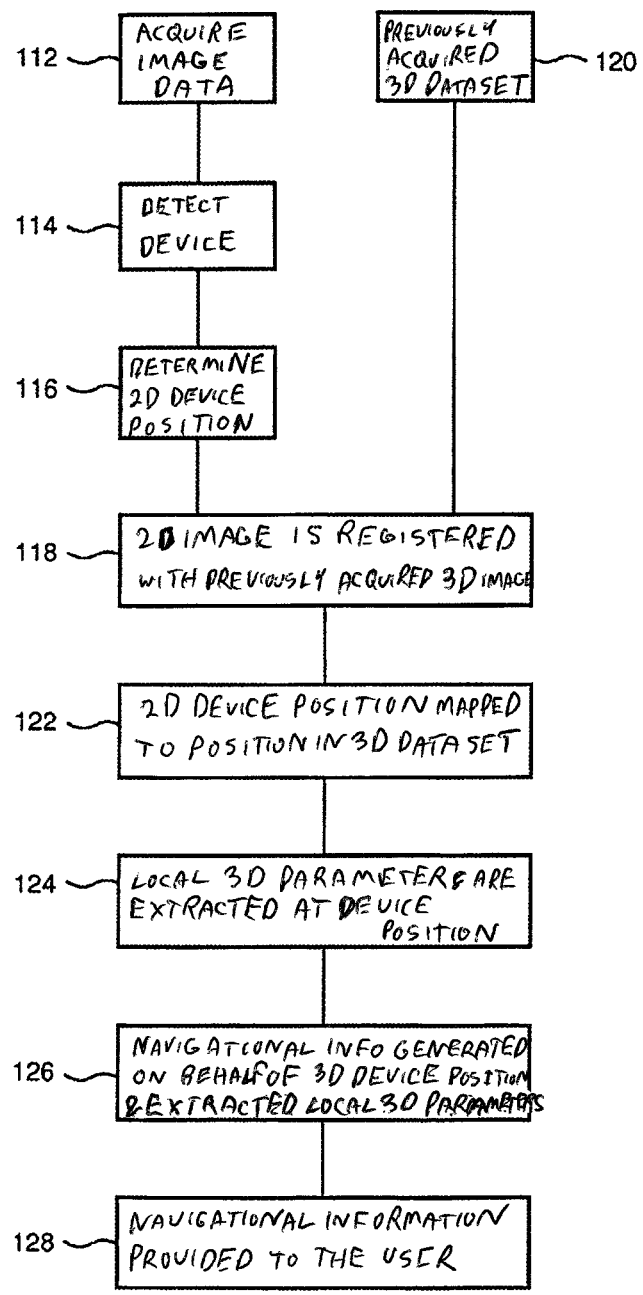
FIG. 2 schematically shows the basic steps of a method for navigating an interventional device according to the invention.

FIG. 1 schematically shows a system 10 for navigating an interventional device 12 within a tubular structure of an object, for example a patient 13. As an example, the interventional device is a guide-wire for percutaneous coronary interventions. The guide wire has a tip, indicated with reference number 14, but not further shown. The system 10 comprises an X-ray image acquisition device 16 with a source of X-ray radiation 18 provided to generate X-ray radiation. A table 20 is provided to receive a subject to be examined, for example the patient 13. Further, the X-ray image acquisition device 16 comprises a detection module 22 located opposite the source of X-ray radiation 18, i.e. during the radiation procedure, the subject or patient 13 is located between the source of X-ray radiation 18 and the detection module 22. The latter is sending data to a control unit or processing unit 24 connected to the X-ray image acquisition device 16 by a cable connection 26. Of course, the cable connection 26 can also be provided in form of a wireless connection (not shown). The interventional device 12 is connected to an interface 28, which connection is not shown in FIG. 1 and which can be implemented as a wire-based or as a wireless connection. The interface 28 is connected to the processing unit 24 and the image X-ray image acquisition device 16 by connections 29 and 30 respectively. Further, a display 32 is connected to the processing unit 24.

The X-ray image acquisition device 16 is provided as a so-called C-type X-ray image acquisition device where the X-ray source 18 and the detection module 16 are arranged on opposing ends of a C-arm 33. The C-arm is rotatably mounted around a horizontal axis indicated as Z-axis. The C-arm can further be rotated in a circular or semicircular form indicated by arrow 34. Further, according to the example shown, the C-arm 33 is mounted to a support 36 suspended from a ceiling 40, wherein the support is rotatable around a vertical axis indicated as X-axis. Thus, X-ray images can be acquired from different directions of different regions of interest of the patient 13.

The interface device 28 is arranged to input information by the user.

It is noted that the example shown as a C-type X-ray image acquisition device, although the invention also relates to other types of X-ray image acquisition devices, such as CT systems. Of course, as an X-ray source a much more simplified C-arm device can be used than the one shown in FIG. 1.

The X-ray image acquisition device 16 is adapted to acquire 2D X-ray fluoroscopy image data in one projection geometry of a region of interest of the tubular structure, in the case shown, of a region of interest of the patient 13.

The processing unit 24 is adapted to detect the interventional device 12 in the 2D X-ray image and to determine the 2D position of the interventional device 12 in the 2D X-ray image. The processing unit 24 is further adapted to register the at least one 2D X-ray image with a previously acquired 3D data set of the region of interest of the patient 13.

The previously acquired 3D data set is stored in a memory (not shown) of the processing unit 24.

The processing unit 24 is further adapted to map the determined 2D position of the interventional device 12 to a position in the 3D data set and to extract local 3D parameters of the tubular structure, for example the vessel structure of the patient, at the position of the interventional device 12. The processing unit 24 is further adapted to generate navigational information on the half of the determined 3D position of the interventional device 12 and the extracted local 3D parameters.

The interface 28 is adapted to provide the navigational information to the user.

The procedure according to the invention to be used with the above described system 12 is described in more detail below.

As can be seen from FIG. 1, the method for navigating the interventional device 12 within a tubular structure of an object, for example the vessel structure of the patient 13, comprises the following steps. First, in an acquisition step 112, 2D X-ray fluoroscopy image data 113 is acquired in one projection geometry of a region of interest of the tubular structure. Second, in a detection step 114, the interventional device 12 is detected in the 2D X-ray image acquired in acquisition step 112. Then, in a determining step 116, the 2D position of the interventional device 12 is determined in the 2D X-ray image. Next, in a registration step 118, the at least one 2D X-ray image is registered with a previously acquired 120 3D data set 121 of the region of interest of the tubular structure. Next, in a mapping step 122, the determined 2D position of the interventional device 12 is mapped to a position in the 3D data set 121. Next, in an extraction step 124, local 3D parameters 125 of the tubular structure are extracted at the position of the interventional device 12. Further, in a generating step 126, navigational information 127 is generated on behalf of the determined 3D position of the interventional device 12 and the extracted local 3D parameters 125. Then, in a providing step 128, the navigational information 127 is provided to the user.

For example, navigating the interventional device 12 comprises guiding the user, for example a physician such as a surgeon, performing a medical procedure.

For example, the 2D X-ray fluoroscopy image data 113 comprises a sequence of two images with the same projection geometry. The 3D position is mapped 122 by extracting a determined point of the interventional device 12 in the two 2D images.

As an example, one point on the interventional device 12 in projection correspond to a line in 3D space and the device 12 moves between two projections, for example during two X-ray fluoroscopy images. The line in space potentially may be located in several segments of the tubular structure, such as vessels of the patient 13. When more points are acquired, for example in a temporal or spatial manner, ambiguity is removed by determining which segment or vessel has the highest probability to enclose the device 12 (not further shown in detail).

As an example, the one projection geometry is a monoplane X-ray fluoroscopy acquisition.

It is noted, that according to the exemplary embodiment, the interventional device 12 lies within a segment of the tubular structure throughout the navigational procedure. Hence, the device 12 can only lie within a couple of possible tubular segments. For example, the probability is maximized by the number of intersections of determined device-originating 3D lines and tubular segments, wherein the intersections correspond to points.

The device 12 has a tip and the tip is localized in the tubular structure complexity with an accuracy of about or less than the tubular width, unless the device 12 is bent and is leaning against either side of the tubular segment. The tip is localized in the tubular structure complexity in the length direction of the tubular segment and not within the width direction.

Needless to say, but the interventional device 12 is at least partially radiopaque to X-rays such that it can be detected in X-ray images. For example, the interventional device is a guide wire. As another example, the interventional device can comprise a biopsy needle or the interventional device 12 is a balloon and stent system for stenosis or aneurysm treatment. It can also be a coil or a flow diverter. It can be any kind of endo-prosthesis, steering device, endo-protection device or measuring device.

In general, the tubular structure such as a vessel structure, has a sparse structure such that the tubular structure provides a few locations in space for the interventional device 12 to be enclosed within the tubular structure.

The 3D data set 121 is, for example, created from acquired 2D projections, for example X-ray angiograms. For example, the 2D projections for generating the 3D data set are acquired in form of rotational angiographic scan.

According to another exemplary embodiment, not further shown, the 3D data set or 3D representation is acquired from a CT scanner, an MRI system, ultrasound system or the like.

In the registration step 118, the at least one 2D X-ray image is registered such that the spatial orientation and position of the 3D volume of the 3D data set 121 corresponds to the spatial orientation and position of the tubular structure of the object of interest in the X-ray radiation. For example, for registration, ridgeness information in the 2D image and in the 3D volume is matched. In the case of weak motions, such as in the case of Neuro interventions, only geometrical information can be used for this registration process.

The method according to the invention provides the advantage, that according to an exemplary embodiment, the 2D device position and related 3D position are continuously tracked during the navigation process and navigational information 127 is provided 128 to the user in real-time.

For example, the local 3D parameters 125 comprise parameters of the tubular segment of the tubular structure surrounding the interventional device 12.

For example, this refers to the vicinity of the interventional device 12 or, in other words to a spatial region around the interventional device 12. For example, the extension of the spatial region is predetermined, for example according to the chosen device or set by a user.

Figure 3:
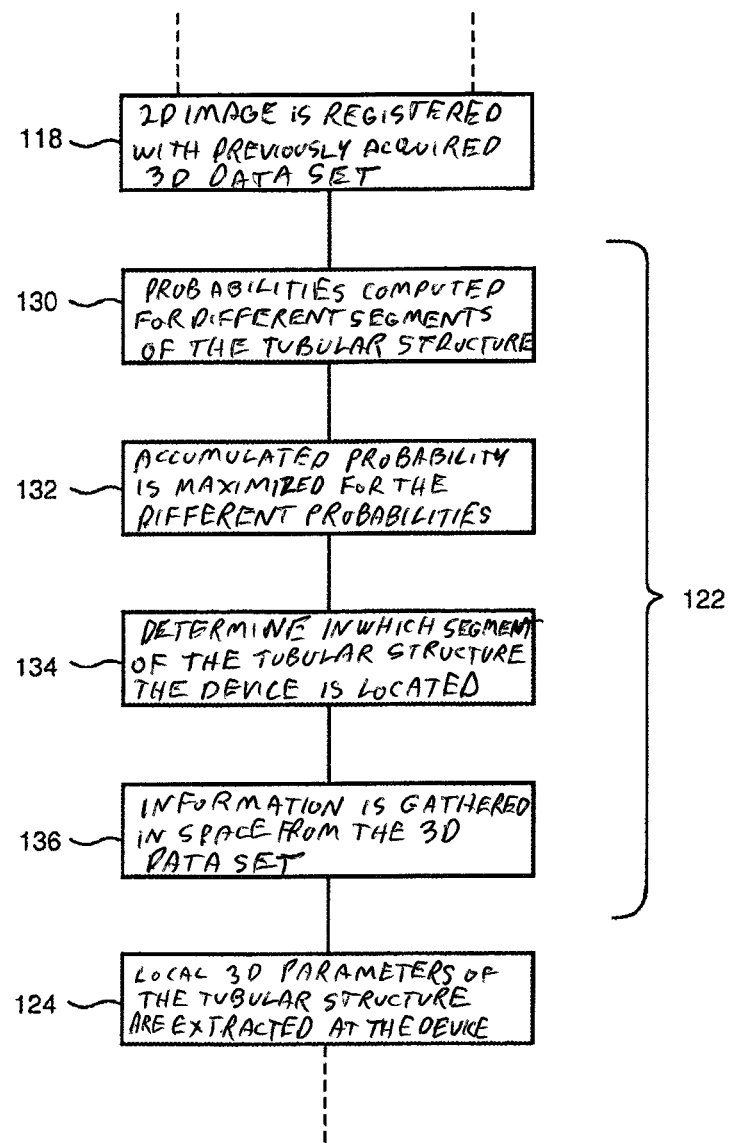
FIG. 3 schematically shows further sub-steps of a further exemplary embodiment of the method of FIG. 2.

According to another exemplary embodiment of the method described above, the step of mapping 122 comprises a computation step 130 where probabilities are computed for different segments of the tubular structure, as indicated in FIG. 3. Then, in a maximizing step 132, accumulated probability is maximized from the different probabilities to determine 134 in which segment of the tubular structure the device may be located. Further, on behalf of the accumulated probability, information is gathered 136 in space from the 3D data set 121.

As an example, not further shown in detail, a device, which is pointwise visible under X-ray fluoroscopy is temporarily detected as two different points. According to this embodiment, in the step of mapping, probability are computed for the points to be located in a number of segments of the tubular structure and the probabilities are maximized to reduce the number of segments and a segment with the highest probability is determined to be enclosing the device.

Figure 4:
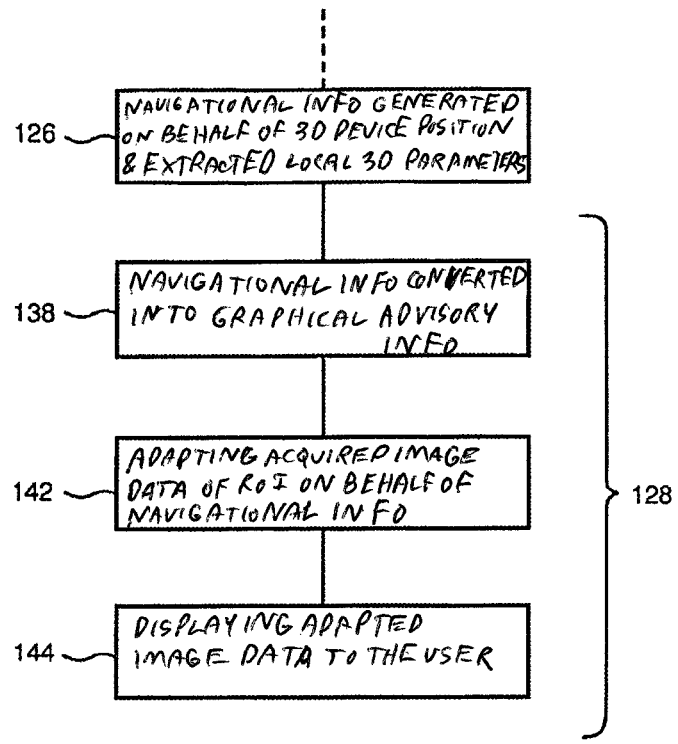
FIG. 4 schematically shows further sub-steps of the method of FIG. 2.

According to a further exemplary embodiment illustrated in FIG. 4, before the providing step 128, the navigational information 127 is converted 138 into graphical advisory information 140. The providing step 128 comprises adapting 142 acquired image data of the region of interest on behalf of the navigational information and displaying 144 the adapted image data to the user.

Figure 5:
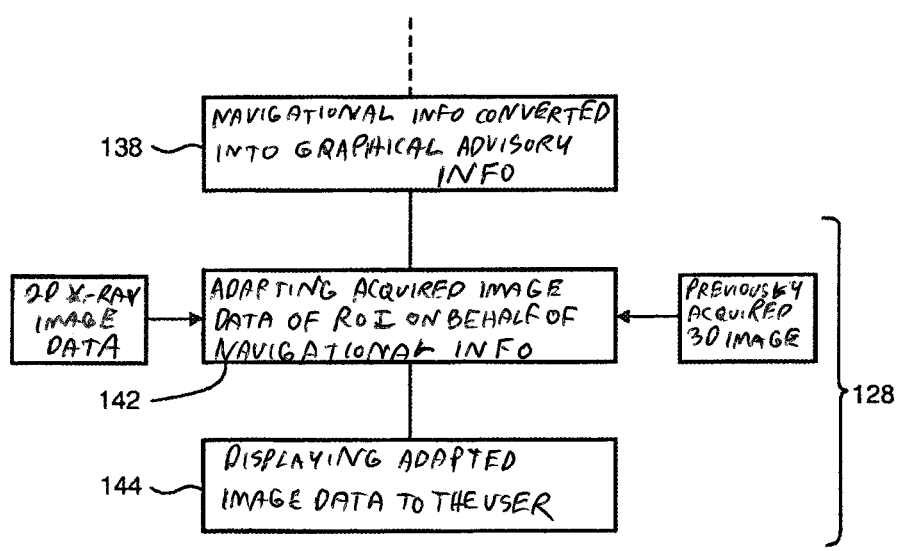
FIG. 5 schematically shows further sub-steps of a further exemplary embodiment of the method of FIG. 2.

According to one example illustrated in FIG. 5, the 2D X-ray image data 113 is transformed into enhanced 2D image data 143a by superimposing the graphical advisory information 140 with a 2D X-ray image data 113 and the enhanced 2D image data 143a is displayed 144 to the user.

According to another exemplary embodiment, 3D image data is generated from the previously acquired 3D data set 121 and the 3D image data is transformed into enhanced 3D image data 143b by integrating the graphical advisory information 140. The enhanced 3D image data 143b is displayed 144 to the user. (see also FIG. 5)

Figure 6:
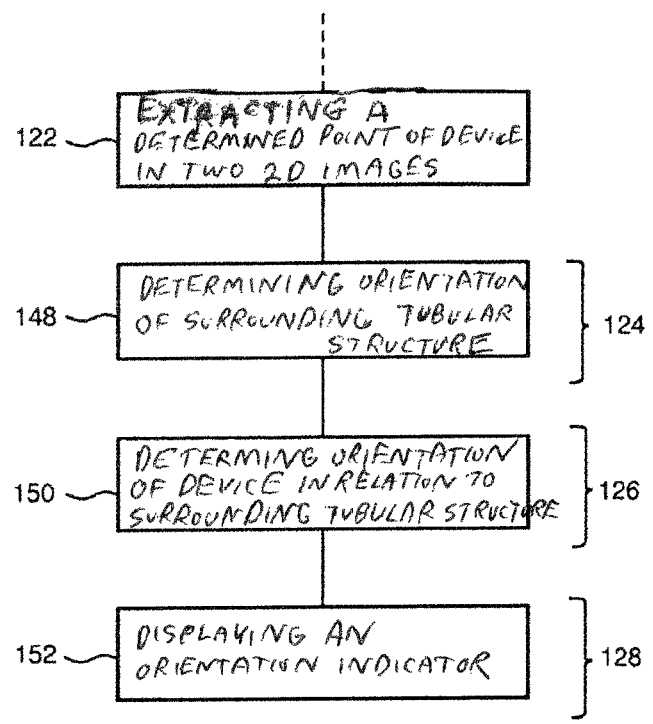
FIG. 6 schematically shows a further exemplary embodiment of the method of FIG. 2.

According to a further exemplary embodiment shown in FIG. 6, the extracting step 124 comprises determining 148 the orientation of the surrounding tubular structure. The generating step 126 comprises determining 150 the orientation of the device 12 in relation to the surrounding tubular structure. Further, the providing step 128 comprises displaying 152 an orientation indicator 154.

For example, the orientation indicator 154 is a depth indicator indicating the depth of the tubular structure.

As a further example, the orientation indicator 154 is an orientation vector.

Figure 7:
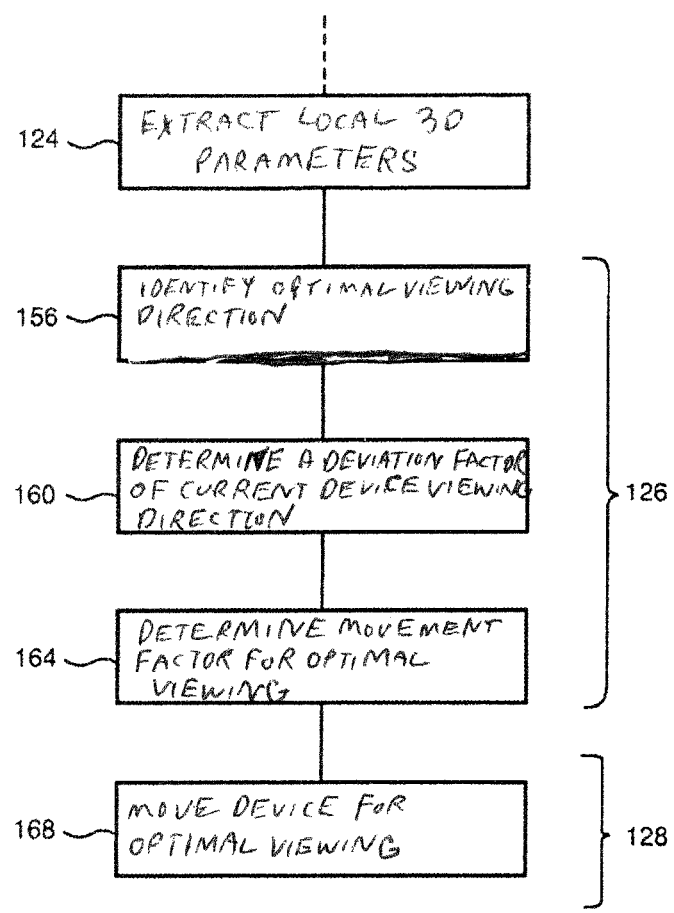
FIG. 7 schematically shows further sub-steps of a further embodiment of the method of FIG. 2.

According to a further exemplary embodiment of the method according to the invention, shown in FIG. 7, the generating step 126 comprises identifying 156 optimal viewing direction 158 for the segment of the tubular structure surrounding the interventional device 12. Then, in a determining step 160, a deviation factor 162 of the current viewing direction of the X-ray imaging device 16 in relation to the optimal viewing direction 158 is determined. Next, in another determining step 164, a movement factor 166 is determined for optimal viewing. The providing step 128 comprises moving 168 the X-ray imaging device 16 for optimal viewing.

For example, the optimal viewing direction 158 is identified for the determined 3D position of the interventional device 12 with respect to the tubular structure.

For example, the X-ray imaging device 16 and the object, that is the patient 13 are moved in relation to each other according to the determined movement factor to acquire further 2D X-ray fluoroscopy image data. For example, when using a C-arm, the C-arm provides for rotational movement and the table 20 is movable in a longitudinal direction to provide movement in this direction. Of course, the table can also be movable in a direction perpendicular to the longitudinal axis to provide a system with movement possibilities in all directions.

In an optimal viewing direction, foreshortening of the tubular structure at the location of the device position is minimal. According to another example, in an optimal viewing direction, overlap of the tubular structure at the location of the device position is minimal.

According to a further exemplary embodiment, that can of course be combined with the above-mentioned embodiments, in an optimal viewing direction, the X-ray dose to the patient and/or the clinical staff is minimal.

According to an exemplary embodiment, not further shown, the optimal viewing angle is defined by different parameters which parameters are being weighed differently depending on the phase of the interventional procedure. For example, during guide wire navigation, the dose parameters have the largest weight whereas during lesion treatment, foreshortening and overlap have the largest weight.

Figure 10:
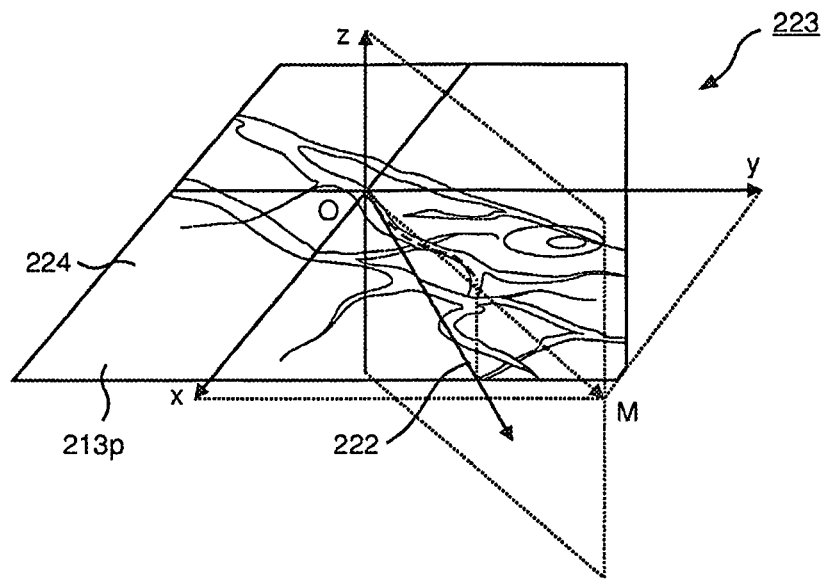
FIG. 10 shows an enhanced 2D X-ray image with one exemplary embodiment of navigational information provided to the user.
Figure 11:
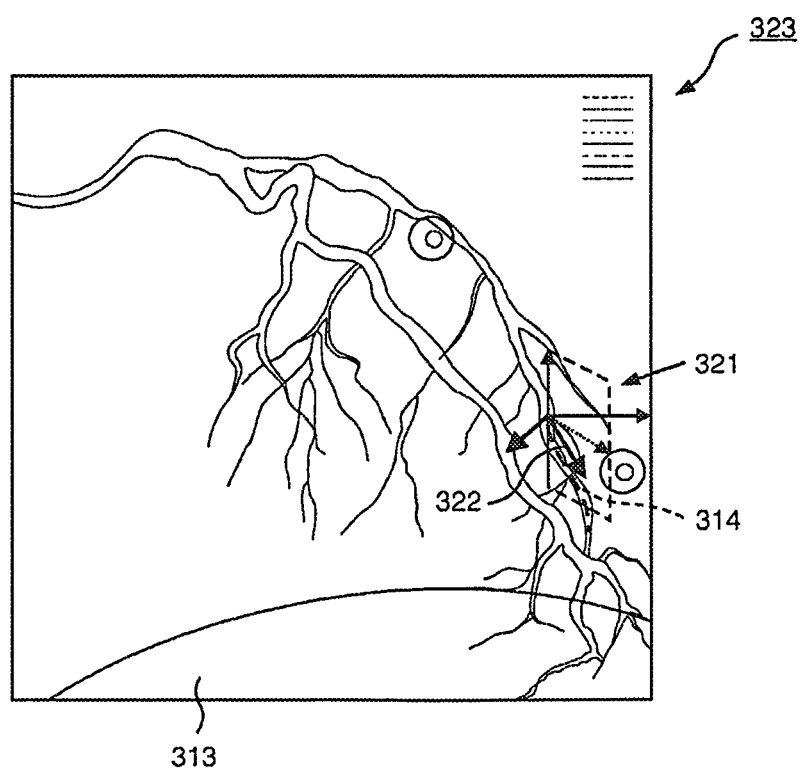
FIG. 11 schematically shows a further exemplary embodiment of the navigational information provided to the user.
Figure 12:
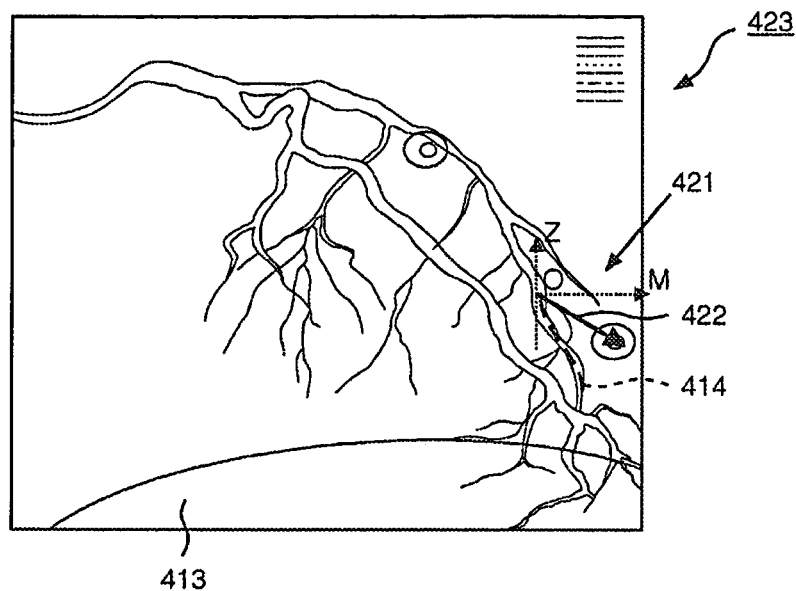
FIG. 12 schematically shows a further exemplary embodiment of the navigational information provided to the user.

Further, FIGS. 10 to 12 schematically show different examples for navigational information being provided 128 to the user.

Figure 8:
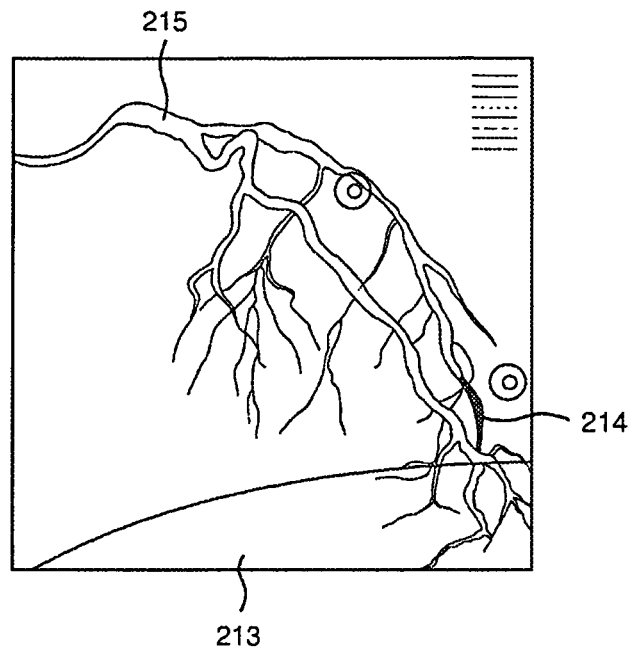
FIG. 8 schematically shows an acquired 2D X-ray fluoroscopy image with a detected device.

FIG. 8 schematically shows an acquired 2D X-ray image 213 with a device 212 of which the device tip 214 is detected and indicated with a graphical marker. The X-ray image shows anatomical information about the object, e.g. the patient 13. As can be seen, the X-ray image shows a part of a tubular structure, i.e. a vessel structure 215. Depending on the type of procedure, the tip can also be indicated in white, colour or in a dotted line, whatever provides the best perceptibility.

Figure 9:
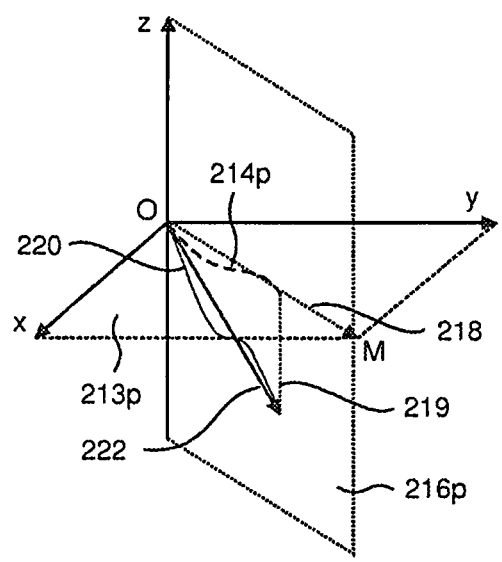
FIG. 9 schematically shows an image plane with the device of FIG. 8 in relation to a device plane.

For a better understanding, FIG. 9 schematically shows a perspective view of an image plane 213p in a geometrical coordinate system indicated by a X-axis, a Y-axis and a Z-axis. The image plane 213p in which the image 213 is acquired is defined by the X-axis and the Y-axis. In other words, the image 213 is the view from so to speak above under some tilted viewing in FIG. 9. The device tip 214 as seen in the image plane 213p is indicated with a dotted line 214p. The device tip 214 is located in a plane being defined as device plane 216p. The device plane 216p is defined by the Z-axis for indicating the depth in the image and a vector 218 starting at O, which is the starting point of the device tip 214 in the image plane 213p, which vector is directed towards M as a line arranged in the horizontal plane 213p including the front end of the tip 214. The actual device is indicated by a line 220. As can be seen, the line 214p is a projection of the device tip line 220 in the horizontal plane 213p, indicated by a connecting line 219 connecting the tip in projection and the tip in its real depth orientation. The depth vector of the device tip 214 is indicated with a vector 222.

The device plane follows the device when moving the device 12 in relation to the patient 13.

This information of the depth direction of the device tip 214 serves as the basis for the navigational information to be provided to the user.

To provide the user with the depth information for steering the device 212, FIG. 10 shows an exemplary embodiment in which the 2D X-ray image 213 is warped to a warped 2D image 224 be arranged in the image plane 213p. The warped image 224 provides the same information as a real-world image to the clinician, only in a distorted or warped way, thus giving the impression of a spatial or 3D arrangement without leaving the graphical means used in 2D images. The coordinate system XYZ, the indication of the image plane and the indication of the device plane provide a good impression of the orientation of the device tip 214 together with depth vector 222. Hence, FIG. 10 shows an enhanced 2D image 223 as navigational information.

Even better information perception can be achieved when applying a certain opacity to the layer of the 2D image (not shown). Then, a better differentiation is possible between a device pointing upwards out of the image plane and a device pointing downwards (as in the figure).

According to an exemplary embodiment (not shown), colors are used for the coordinate system, the image plane and the device plane as well as for the device tip and the depth vector.

Another exemplary embodiment is shown in FIG. 11 where a device tip 314 is detected in an acquired 2D X-ray fluoro image 313, the device tip indicated by a white line for example. Of course, on a color display, the device tip can be shown in color, for example in red. A miniature version of the coordinate system of FIG. 9, or pictogram 321, is shown within the image 313 thus providing an enhanced 2D image 323. The actual orientation of the device in relation to the image plane is indicated with a depth vector 322 acting as navigational information.

Another exemplary embodiment is shown in FIG. 12. Instead of the 3D coordinate system, a further reduced pictogram 421 is shown in an X-ray image 413, the pictogram 421 comprising a Z-axis and the axis O-M within the image plane, i.e. the view is perpendicular to the image plane itself. This navigational information is shown within a 2D X-ray image 413 where the device tip is detected and indicated with a white marked line 414, which, of course, can also be displayed in color. The depth orientation of the device tip is indicated by a depth vector 422 in relation to the reduced graphical coordinate system. Accordingly, an enhanced 2D image 423 is provided to the user.

Figure 13:
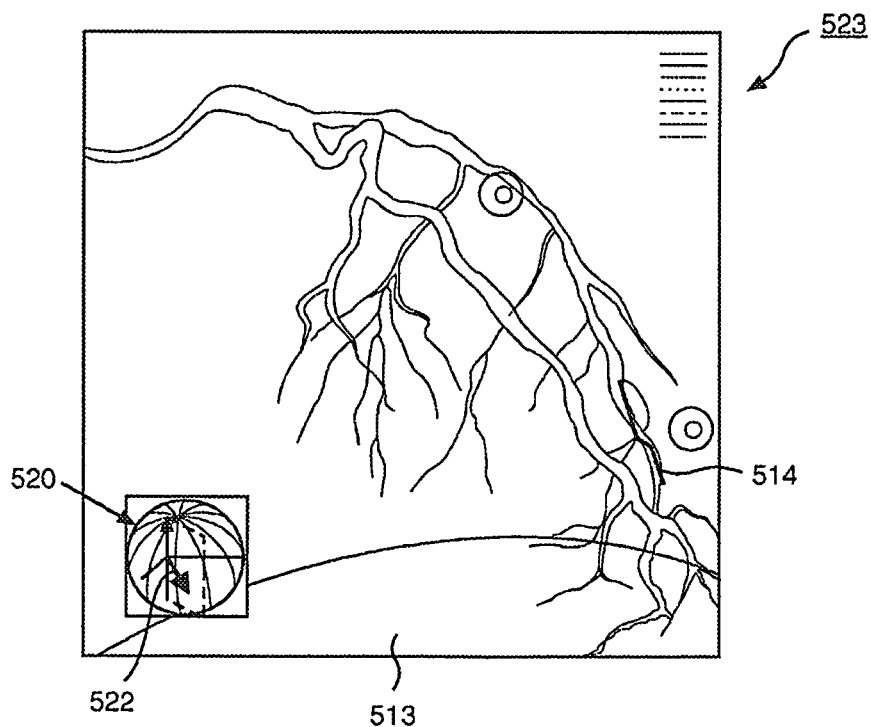
FIG. 13 schematically shows a further exemplary embodiment of the navigational information provided to the user.
Figure 14:
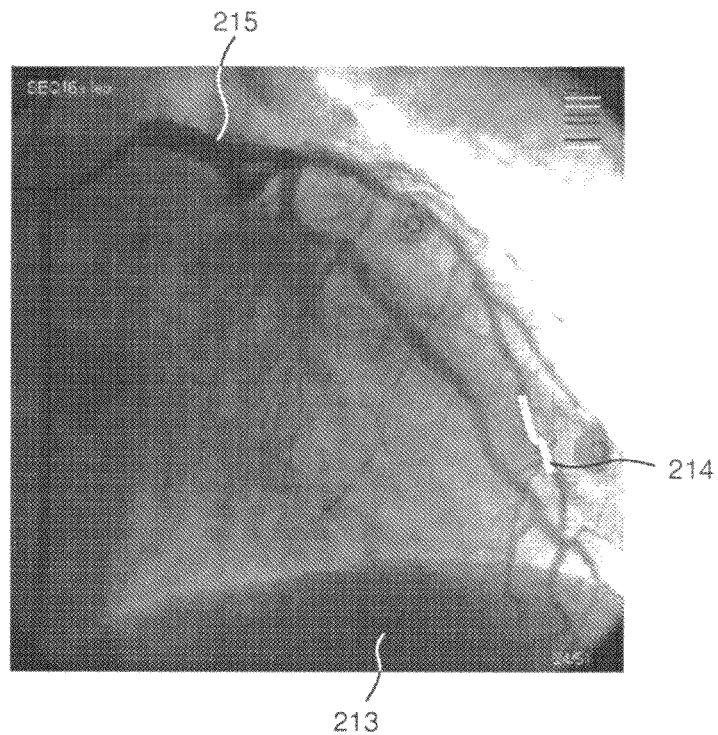
FIGS. 14 to 18 show FIGS. 8, 10, 11, 12 and 13 with an X-ray image instead of the schematic representation of an X-ray image for better understanding.
Figure 15:
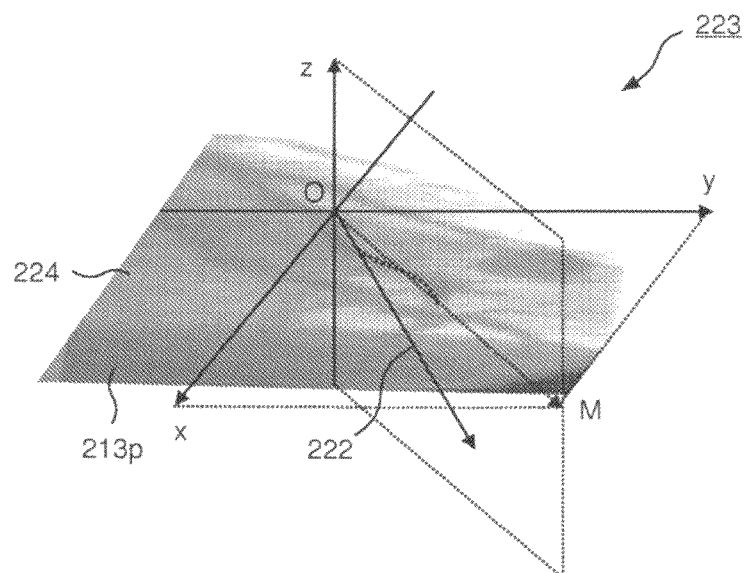
Figure 16:
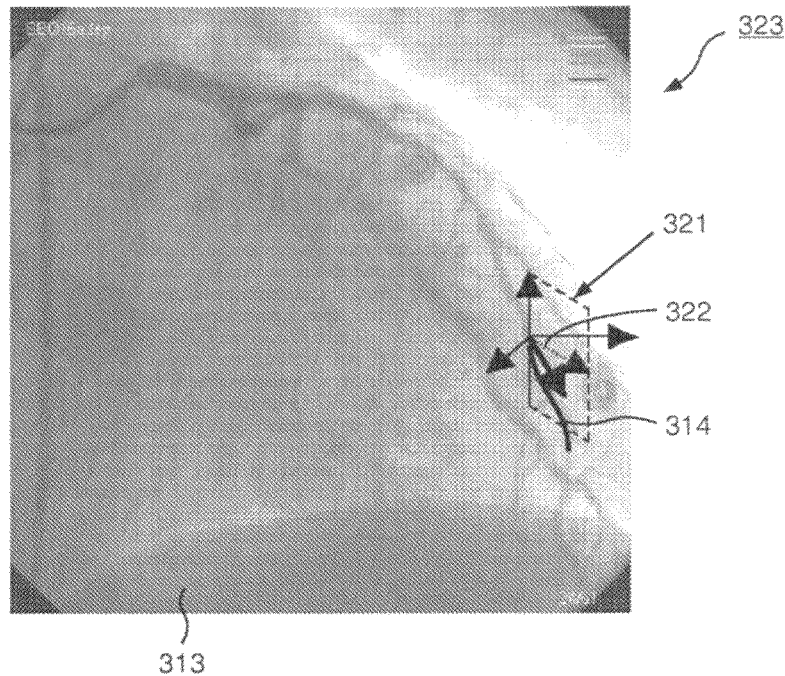
Figure 17:
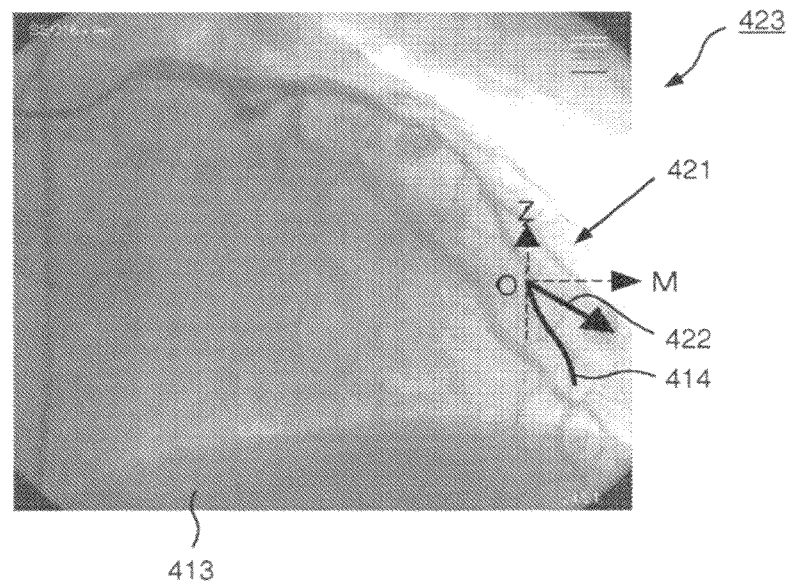
Figure 18:
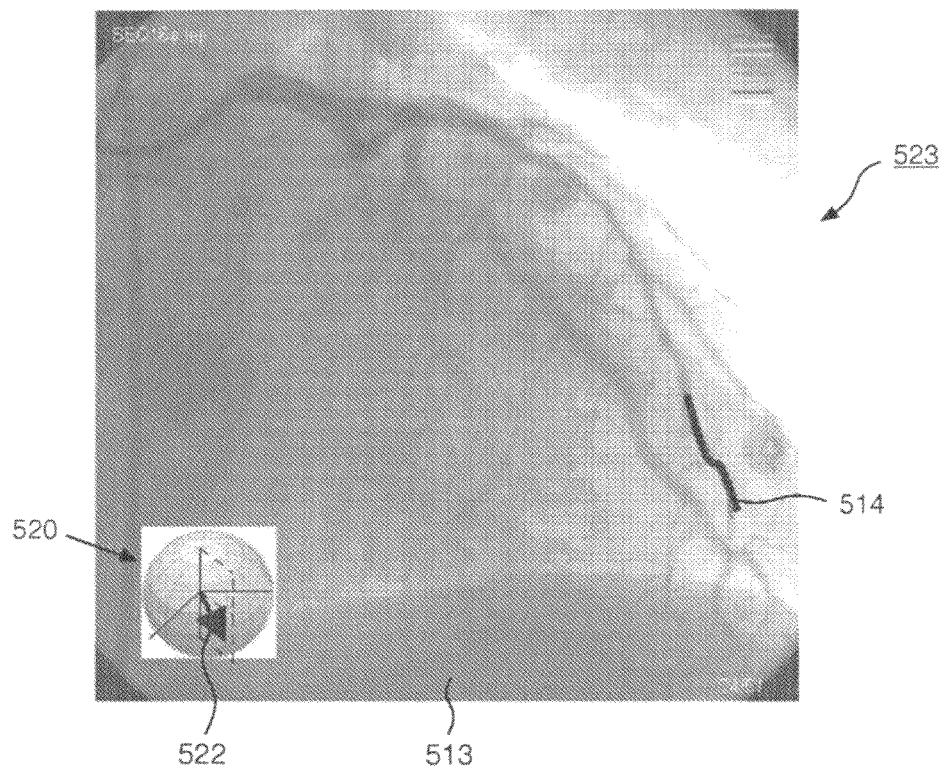

Another exemplary embodiment is shown in FIG. 13. The device tip is indicated with a color-coded marker 514. The color-coding is relating to a color space as, for example known from Johannes Itten or Philipp Otto Runge. Basically, a spectrum of colors is associated with surface parts of a sphere. A direction vector, or orientation vector, arranged in space according to the determined orientation will thus point at different parts with different colors. Hence, the depth vector as described above, is replaced by a color depending on its direction. In one exemplary embodiment, the color only refers to a vector direction within a plane vertical to the image plane. In another exemplary embodiment, the color also takes the horizontal angle into account, which of course is also visible on the image. For facilitating the understanding, a color coded sphere or band-like color coded space 520 is shown as a pictogram within the 2D X-ray image 513. The orientation in space is indicated with an arrow 522 pointing at the color in which the device tip 514 is shown. Accordingly, an enhanced 2D image 523 is provided to the user.

According to a reduced exemplary embodiment of the one described above, a simple color coding of [−pi/2, +pi/2] is provided, because the device direction is already known in projection. As an example, a color bar is provided and the tip is directly colored with the respective color.

According to another exemplary embodiment, but which is not further shown, 3D image data is generated from the previously acquired 3D dataset. The 3D image data is transformed into enhanced 3D image data by integrating the graphical advisory information in a similar way as described above for the enhanced 2D X-ray images.

According to a further exemplary embodiment, not further shown, one of the above-mentioned examples is provided in colour for further or more detailed navigational information.

By providing a system and a method according to the invention, the user is provided with easily comprehensible navigation information in a graphical world, that is in the 2D X-ray fluoroscopy images, which most clinicians are familiar with. Thus, the user is provided with the real world information he wishes to rely upon, that is the information provided in the actual X-ray fluoroscopy image, plus additional navigation information facilitating the steering or navigation of the interventional device within the tubular structure.

FIGS. 14 to 18 show FIGS. 8, 10, 11 and 12 respectively with an X-ray image instead of the schematic representation of an X-ray image for better understanding. For better visibility, the device tip is indicated with a white line in FIG. 14.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

A computer program may be stored and/or distributed on a suitable medium, such as an optical storage medium or a solid state medium supplied together with or as part of other hardware, but may also be distributed in other forms, such as via the interne or other wired or wireless telecommunication systems.

Any reference signs in the claims should not be construed as limiting the scope.

The invention claimed is:

1. A system for navigating an interventional device a tubular structure of an object; comprising:
   an X-ray image acquisition device;
   a processing unit; and
   an interface;
   wherein the X-ray image acquisition device is configured to acquire two-dimensional (2D) X-ray fluoroscopy image data in one projection geometry of a region of interest of the tubular structure;
   wherein the processing unit is configured:
      to detect the interventional device in the 2D X-ray image;
      to determine the 2D position of the interventional device in the 2D X-ray image;
      to register the at least one 2D X-ray image with a previously acquired three-dimensional (3D) dataset of the region of interest of the tubular structure;
      to map the determined 2D position of the interventional device to a position in the 3D dataset;
      to extract local 3D parameters of the tubular structure at the position of the interventional device; and
      to generate navigational information on behalf of the determined 3D position of the interventional device and the extracted local 3D parameters; and
   wherein the interface is configured to provide the navigational information to the user.

2. The system according to claim 1, wherein the processing unit is configured:
   to convert the navigational information into graphical advisory information; and
   to adapt acquired image data of the region of interest on behalf of the navigational information;
   said system comprising a display to display the adapted image data to the user.

3. The system according to claim 1, comprising a display, wherein the processing unit is configured:
   to determine the orientation of the surrounding tubular structure; and
   to determine the orientation of the interventional device in relation to the surrounding tubular structure; and
   wherein the display is configured to display an orientation indicator.

4. The system according to claim 1, wherein the processing unit is configured to:
   identify an optimal viewing direction for the segment of the tubular structure surrounding the interventional device;
   to determine a deviation factor of a current viewing direction of the X-ray imaging devices in relation to the optimal viewing direction; and
   to determine a movement factor for optimal viewing; and wherein the X-ray image acquisition device is on figured to be moved in relation to the object for optimal viewing.

5. A method for navigating an interventional device within a tubular structure of an object, comprising the following steps:
   a) acquiring two-dimensional (2D) X-ray fluoroscopy image data in one projection geometry of a region of interest of the tubular structure;
   b) detecting the interventional device in the 2D X-ray image;
   c) determining the 2D position of the interventional device in the 2D X-ray image;
   d) registering the at least one 2D X-ray image with a previously acquired three-dimensional (3D) dataset of the region of interest of the tubular structure;
   e) mapping the determined 2D position of the interventional device to a position in the 3D dataset;
   f) extracting local 3D parameters of the tubular structure at the position of the interventional device;
   g) generating navigational information on behalf of the determined 3D position of the interventional device and the extracted local 3D parameters; and
   h) providing the navigational information to the user.

6. The method according to claim 5, wherein step e) comprises,
   computing probabilities for different segments of the tubular structure; and
   maximizing accumulated probability from the different probabilities to determine in which segment of the tubular structure the interventional device is located;
   wherein on behalf of the accumulated probability information is gathered in space from the 3D dataset.

7. The method according to claim 5, wherein before step h), the navigational information is converted into graphical advisory information and wherein step h) comprises adapting acquired image data of the region of interest on behalf of the navigational information and displaying the adapted image data to the user.

8. The method according to claim 5, wherein the 2D X-ray image data is transformed into enhanced 2D image data by superimposing the graphical advisory information with the 2D X-ray image data; and wherein the enhanced 2D image data is displayed to the user.

9. The method according to claim 5, wherein 3D image data is generated from the previously acquired 3D dataset and wherein the 3D image data is transformed into enhanced 3D image data by integrating the graphical advisory information; and wherein the enhanced 3D image data is displayed to the user.

10. The method according to claim 5, wherein step f) comprises determining the orientation of the surrounding tubular structure; wherein step g) comprises determining the orientation of the device in relation to the surrounding tubular structure; and wherein step h) comprises displaying an orientation indicator.

11. The method according to claim 5, wherein step g) comprises identifying an optimal viewing for the segment of the tubular structure surrounding the interventional device; determining a deviation factor of a current viewing direction of the X-ray imaging device in relation to the optimal viewing direction; and determining a movement factor for optimal viewing; and wherein step h) comprises moving the X-ray imaging device in relation to the object for optimal viewing.

12. A non-transitory computer readable medium embodying a program for navigating an interventional device within a tubular structure of an object, said program having instructions executable by a processor for performing a plurality of acts, among said plurality there being the acts of:
   a) acquiring two-dimensional (2D) X-ray fluoroscopy image data in one projection geometry of a region of interest of the tubular structure;
   b) detecting the interventional device in the 2D X-ray image:
   c) determining the 2D position of the interventional device in the 2D X-ray image;
   d) registering the at least one 2D X-ray image with a previously acquired three-dimensional 3D dataset of the region of interest of the tubular structure;
   e) mapping the determined 2D position of the interventional device to a position in the 3D dataset;
   f) extracting local 3D parameters of the tubular structure at the position of the interventional device;
   g) generating navigational information on behalf of the determined 3D position of the interventional device and the extracted local 31) parameters; and
   h) providing the navigational information to the user.

* * * * *